United States Patent [19]

Sakurai et al.

[11] Patent Number: 4,788,219
[45] Date of Patent: Nov. 29, 1988

[54] ANTIMETASTATIC AGENT

[75] Inventors: Yoshio Sakurai, Mitaka; Takashi Tsuruo, Tokyo, both of Japan

[73] Assignees: Cancer Institute, Japanese Foundation for Cancer Research; Eisai Co., Ltd., both of Tokyo, Japan

[21] Appl. No.: 4,005

[22] Filed: Jan. 16, 1987

Related U.S. Application Data

[63] Continuation of Ser. No. 725,027, Apr. 19, 1985, abandoned.

[30] Foreign Application Priority Data

Apr. 20, 1984 [JP] Japan .................................. 59-79632

[51] Int. Cl.⁴ .......................................... A61K 31/275
[52] U.S. Cl. .................................................. 514/523
[58] Field of Search ........................................ 514/523

[56] References Cited

PUBLICATIONS

Chemical Abstracts 98:119278k (1983).
Chemical Abstracts 101:163325c (1984).

Primary Examiner—Jerome D. Goldberg
Attorney, Agent, or Firm—Flynn, Thiel, Boutell & Tanis

[57] ABSTRACT 5-((3,4-dimethoxyphenetyl)methylamino)- 2-(3,4-dimethoxy-phenyl)-2-isopropylvaleronitrile or a pharmaceutically acceptable salt thereof is effective to prevent metastasis of cancer.

7 Claims, No Drawings

ANTIMETASTATIC AGENT

This is a continuation of application Ser. No. 725,027, filed Apr. 19, 1985 now abandoned.

This invention relates to a novel agent for preventing metastasis of cancer, i.e. an antimetastatic agent.

More particularly it relates to an antimetastatic agent comprising 5-[(3,4-dimethoxyphenethyl)methylamino]-2-(3,4-dimethoxyphenyl)-2-isopropylvaleronitrile of the formula

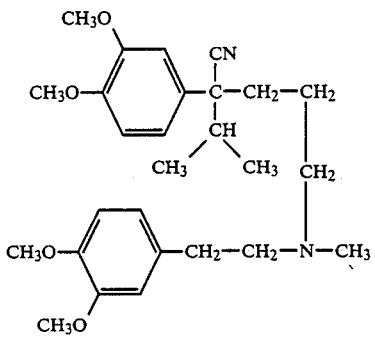

or a salt thereof as an active ingredient.

In the recent survey statistics cancer has occupied the first place in death causes in Japan, instead of cerebrovascular diseases. 24% of deaths, i.e. one among four, died of cancer. This mortal disease causes indescribable pain not only to the body but to the mind of a patient. In addition, cancer most frequently attacks those in the prime of life (i.e. in fourties to fifties) when the victims are playing important roles both in society and in their own homes so that their families also suffer from serious mental and economic damages.

Therefore various studies to reveal the fundamental cause of cancer and to establish epoch-making processes for the treatment and diagnosis thereof have been carried out all over the world to thereby gain ascendancy over cancer step by step. These studies have brought about significantly improved treatments and diagnosis of cancer, so that it can be completely cured in most cases if detected early enough.

Even if the original tumor is completely removed by early diagnosis followed by a surgical operation, however, tumor cells would metastasize to another organ at the time of the diagnosis in more than half the cases. That is, many patients died of metastasis of cancer. Accordingly it is one of the most important problems in the treatment of cancer to prevent its metastasis.

Metastasis, which is a specific, complicated and important characteristic of cancer, comprises many steps such as liberation of cancerous cells from the primary portion, transfer via blood or lymph vessels, adhesion to a blood or lymph vessel of an organ, infiltration and growth. The metastasis of cancer is an important factor governing the recuperation of a patient. However studies thereon still remain significantly backward since appropriate experimental systems to evaluate the metastasis are quite limited. The mechanism of metastasis has not been clarified and few countermeasures have been established at present.

In order to lower the mortality from cancer, it is a very important problem to prevent and treat the metastasis. Few antimetastatic agents, however, have been known to date.

Under these circumstances, we have tried to develop an agent for preventing metastasis of cancer, i.e. an antimetastatic agent, for a long time and found that verapamil, i.e. 5-[(3,4-dimethoxyphenethyl)methyl]-2-(3,4-dimethoxyphenyl)-2-isopropylvaleronitrile of the following formula or its salt such as hydrochloride would be unexpectedly effective as an antimetastatic agent.

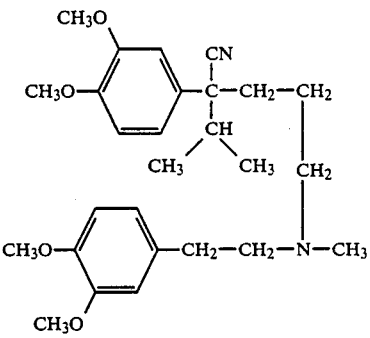

Accordingly it is an object of the present invention to provide a novel antimetastatic agent.

Verapamil of the above formula has been used as a therapeutic agent for ischemic cardiac diseases in treating e.g., stenocardia, coronary arteriosclerosis (chronic ischemic cardiac diseases, silent ischemic cardiac diseases and arteriosclerosis cardiac diseases), and myocardial infraction.

Verapamil hydrochloride has a melting point of 138.5° to 140.5° C. (decomp.).

To further illustrate the present invention, the following examples will be given.

EXAMPLE 1

Effect of verapamil on pulmonary metastasis of B16 melanoma BL-6

B16 melanoma BL-6, isolated by Dr. Hart et al. in U.S.A., is a cell line which infiltrates through a bladder membrane and shows metastatic potential. $5 \times 10^4$ cells of B16 melanoma BL-6 were inoculated into the tail vein of a male C57BL/6J mouse. Verapamil hydrochloride was administered intraperitoneally once a day two days before the inoculation of tumor cells and three days thereafter, that is, six times in total. On the 25th day after the transplantation, the mouse was anatomized to observe the metastasis to thelungs. The degree of the metastasis was evaluated by the number of pulmonary nodules. The evaluated values were represented by range, median and mean+DS. a mark "a" indicates that a significant difference has been observed when compared with a control, that is, p is smaller than 0.05 (Student's t-test). Ten mice were used per a group. Table 1 shows results.

TABLE 1

| Dose of verapamil hydrochloride (mg/kg) | No. of pulmonary nodules | | | | | |
|---|---|---|---|---|---|---|
| | Median | Range | % to control | Mean ± SD | % to control | Significant Difference |
| 30 | 4.5 | 3~9 | 32 | 5.0 ± 1.7 | 29 | a |

TABLE 1-continued

| Dose of verapamil hydrochloride (mg/kg) | No. of pulmonary nodules | | | | | |
|---|---|---|---|---|---|---|
| | Median | Range | % to control | Mean ± SD | % to control | Significant Difference |
| 40 | 12 | 1~19 | 86 | 9.8 ± 6.8 | 56 | a |
| 50 | 9.5 | 2~13 | 68 | 8.0 ± 4.3 | 46 | a |
| Control | 14 | 4~33 | 100 | 17.5 ± 9.3 | 100 | |

EXAMPLE 2

Metastasis of B16 melanoma BL-6 to lungs and lymphonodi $25 \times 10^4$ cells of B16 melanoma BL-6 were transplanted to the right forefoot of a C57BL/6J male mouse. Cancerous cells would spontaneously metastasize to the right nodi lymphatic axillares and lungs with the elapse of time. Verapamil hydrochloride was intraperitoneally administered once a day from the fifth to 16th day (i.e. 11 times) after the transplantation of the cancerous cells. On the 17th day after the transplantation, the right forefoot including the primary tumor was cut off. On the 38th day the mouse was anatomized to determine the number of pulmonary nodules.

Table 2 shows the result.

TABLE 2

| Dose of verapamil hydrochloride (mg/kg) | No. of pulmonary nodules | | | | | |
|---|---|---|---|---|---|---|
| | Median | Range | % to control | Mean ± SD | % to control | Significant Difference |
| 30 | 11 | 3~21 | 147 | 12.3 ± 6.5 | 75 | |
| 40 | 5 | 1~12[a] | 67 | 5.8 ± 3.7 | 35 | |
| 50 | 1.5 | 0~12 | 20 | 3.5 ± 4.3 | 21 | a |
| Control | 7.5 | 1~42 | 100 | 16.5 ± 17.1 | 100 | |

EXAMPLE 3

Effect of verapamil on pulmonary metastasis of highly metastatic clone NL-17 of mouse colonic cancer colon 26 adenocarcinoma $5 \times 10^4$ cells of a highly metastatic cell strain clone NL-17 were transplanted into a vein of a BALB/C female mouse. Verapamil hydrochloride was administered intraperitoneally to the mouse once a day from two days before the inoculation of tumor cells to three days thereafter, i.e. six times in total. On the 23rd day after inoculation, the mouse was anatomized to determine the number of metastatic pulmonary nodules. Results are shown in Table 3.

TABLE 3

| Dose of verapamil hydrochloride (mg/kg) | No. of pulmonary nodules | | | | | |
|---|---|---|---|---|---|---|
| | Median | Range | % to control | Mean ± SD | % to control | Significant Difference |
| 60 | 1 | 0~96 | 2.1 | 13.1 ± 31.3 | 15.6 | a |
| 75 | 1.5 | 0~67 | 3.2 | 18.6 ± 24.5 | 22.1 | a |
| Control | 47.5 | 5~>200 | 100 | 84 ± 71.3 | 100 | |

EXAMPLE 4

Effect of verapamil on pulmonary metastasis of highly metastatic clone NL-22 of mouse colonic cancer colon 26 adnocarcinoma $1 \times 10^6$ cells of a highly metastatic cell strain NL-22 of mouse colonic cancer colon 26 were transplanted into the right forefoot of a BALB/C female mouse. Cancerous cells would spontaneously metastasize to the lungs with the elapse of time. Verapamil hydrochloride was intraperitoneally administered to the mouse once a day from the sixth to 12th day after the transplantation, i.e. six times in total. On the 13th day after the transplantation, the right forefoot including the primary carcinoma was cut off. On the 29th day, the mouse was anatomized to determine the number of pulmonary nodules.

TABLE 4

| Dose of verapamil hydrochloride (mg/kg) | No. of pulmonary nodules | | | | | |
|---|---|---|---|---|---|---|
| | Median | Range | % to control | Mean ± SD | % to control | Significant Difference |
| 50 | 34.5 | 12~55 | 91 | 33.1 ± 14.6 | 59 | |
| 60 | 22.5 | 10~41 | 59 | 23.5 ± 8.5 | 42 | a |
| 75 | 19 | 7~74 | 50 | 27.8 ± 21.8 | 50 | a |
| Control | 38 | 22~126 | 100 | 55.9 ± 31.8 | 100 | |

Examples 1 to 4 as shown above clearly indicate that the verapamil hydrochloride according to the present invention remarkably prevents metastasis of cancer not only in a single experimental system but also in various experimental systems for cancer metastasis in animals.

Accordingly the verapamil according to the present invention is useful as an excellent agent for preventing metastasis of cancer, i.e. an antimetastatic agent.

The dose of the verapamil of the present invention as an antimetastatic agent depends on various factors such as the type of cancer and the condition of the patient. It may be usually administered to an adult orally or parenterally in a dose of 10 to 500 mg once to four times a day without any limitation.

It may be formulated into various forms such as powder, grain, granule, tablet, capsule and injection. Formulation may be carried out in a conventional manner with the use of conventional carriers.

In addition to the use as a therapeutic agent administered to cancerous patients, the verapamil of the present invention is further available in preventing metastasis in those who have received medical treatments such as chemotheraay, endocrinotherapy and immunotherapy, radiotherapy or surgical treatments.

Needless to say, the agent of the present invention may be simultaneously administered with other carcinostatic agents.

Toxicity of the verapamil hydrochloride as used in the present invention will now be shown.

Acute toxicity

Table 5 shows $LD_{50}$ (mg/kg) thereof.

TABLE 5

| Animal | Sex | Oral | Subcutaneous | Intramuscular | Intravenous |
|---|---|---|---|---|---|
| Mouse | Male | 163 | 68 | — | 7.6 |
| Rat | Male | 108 | 107 | 118 | 16 |
|  | Female | 126 | — | — | — |
| Dog | Male and female | >400 | — | 25 | — |

As described above in detail, the verapamil of the present invention is remarkably effective as an antimetastatic agent. Since metastasis is the cause of deaths due to cancer in most cases, the present invention is extremely valuable.

The embodiments of the invention in which an exclusive property or privilege is claimed are defined as follows:

1. A method for the reduction of metastasis in a patient afflicted with cancer consisting essentially of administering to said patient an amount of verapamil or a pharmaceutically salt thereof to reduce the metastasis of cancer cells without treating the cancer per se.

2. A process as claimed in claim 1 in which said cancer cells are metastasizable to the lung.

3. A process as claimed in claim 1 in which the verapamil, or pharmaceutically acceptable salt thereof, is administered intraperitoneally.

4. A process as claimed in claim 1 in which the verapamil or pharmaceutically acceptable salt thereof, is administered to said, orally or parenterally, in a dose of from 10 to 500 mg, from 1 to 4 times a day, in association with a pharmaceutically acceptable carrier.

5. A process as claimed in claim 1 in which said has previously received chemotherapy, radiotherapy or surgical treatment of the cancer.

6. A process as claimed in claim 1 in which the cancer cells are melanoma cells.

7. A process as claimed in claim 1 in which the cancer cells are colon cancer cells.

* * * * *

UNITED STATES PATENT AND TRADEMARK OFFICE
CERTIFICATE OF CORRECTION

PATENT NO. : 4 788 219
DATED : November 29, 1988
INVENTOR(S) : Yoshio SAKURAI et al It is certified that error appears in the above-identified patent and that said Letters Patent is hereby corrected as shown below:

Column 6, line 13; before "lung" insert ---patient's---.
        line 19; change "said, orally" to
           ---said patient, orally---.
        line 22; after "said" insert ---patient---.

Signed and Sealed this

Twenty-seventh Day of June, 1989

Attest:

DONALD J. QUIGG

Attesting Officer      Commissioner of Patents and Trademarks